US008620406B2

(12) United States Patent
Smith et al.

(10) Patent No.: US 8,620,406 B2
(45) Date of Patent: Dec. 31, 2013

(54) MEDICAL DEVICES VISIBLE BY MAGNETIC RESONANCE IMAGING

(75) Inventors: Scott R. Smith, Chaska, MN (US); Steven E. Walak, Natick, MA (US); Lixiao Wang, Long Lake, MN (US); Jan Weber, Maple Grove, MN (US); Sheng-Ping Zhong, Northborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2958 days.

(21) Appl. No.: 10/763,690

(22) Filed: Jan. 23, 2004

(65) Prior Publication Data

US 2005/0165301 A1 Jul. 28, 2005

(51) Int. Cl.
*A61B 5/05* (2006.01)

(52) U.S. Cl.
USPC .......................................... 600/420; 600/431

(58) Field of Classification Search
USPC ......... 600/407, 410, 414, 420, 421, 422, 423, 600/431
See application file for complete search history.

(56) References Cited

U.S. PATENT DOCUMENTS

| 4,963,313 A | 10/1990 | Noddin et al. |
| 4,985,233 A | 1/1991 | Klaveness et al. |
| 4,989,608 A | 2/1991 | Ratner |
| 5,154,179 A | 10/1992 | Ratner |
| 5,352,431 A | 10/1994 | Hashiguchi et al. |
| 5,702,682 A | 12/1997 | Thompson |
| 5,714,110 A | 2/1998 | Wang et al. |
| 5,728,079 A | 3/1998 | Weber et al. |
| 5,744,958 A | 4/1998 | Werne |
| 5,817,017 A | 10/1998 | Young et al. |
| 6,123,920 A | 9/2000 | Gunther et al. |
| 6,207,134 B1 | 3/2001 | Fahlvik |
| 6,264,611 B1 | 7/2001 | Ishikawa et al. |
| 6,280,385 B1 * | 8/2001 | Melzer et al. ............ 600/423 |
| 6,423,296 B1 | 7/2002 | Gunther et al. |
| 6,436,056 B1 | 8/2002 | Wang et al. |
| 6,488,694 B1 | 12/2002 | Lau et al. |
| 6,503,224 B1 | 1/2003 | Forman et al. |
| 6,595,952 B2 | 7/2003 | Forsberg |

(Continued)

FOREIGN PATENT DOCUMENTS

WO          01/75465        10/2001

OTHER PUBLICATIONS

Glowinski et al., "Catheter Visualization Using Locally Induced, Actively Controlled Field Inhomogeneities," MRM 38:253-258 (1997).

(Continued)

*Primary Examiner* — Jonathan G Cwern
*Assistant Examiner* — Amelie R Gillman
(74) *Attorney, Agent, or Firm* — Seager, Tufte & Wickhem, LLC

(57) ABSTRACT

Medical devices that are visible by magnetic resonance imaging (MRI), and optionally, other imaging techniques, are described. In some embodiments, a medical device adapted for insertion into the body includes an elongated shaft and an electrically conductive path extending spirally about a portion of the shaft. The conductive path is capable of being connected to a current source. The medical device can further include one or more contrast agents (such as MRI contrast agents, radiopaque materials, and/or ultrasound visible materials), which can be arranged in a predetermined manner.

1 Claim, 6 Drawing Sheets

(56) References Cited

U.S. PATENT DOCUMENTS

| | | | |
|---|---|---|---|
| 2003/0065267 A1 | 4/2003 | Smith | |
| 2003/0099764 A1 | 5/2003 | Li et al. | |
| 2003/0100830 A1* | 5/2003 | Zhong et al. | 600/431 |
| 2003/0185895 A1 | 10/2003 | Lanphere et al. | |

OTHER PUBLICATIONS

M.E. Ladd, "Active Visualization—MR Profiling," 1998, Intervention Magnetic Resonance Imaging, Berlin Heidelberg, pp. 77-82.

Partial International Search Report received in Application No. PCT/US2005/000315, mailed May 13, 2005.

Douglas A. Devens Jr., "Multilayer Medical Devices", U.S. Appl. No. 10/645,014, filed Aug. 21, 2003.

Zhong et al., "Medical Devices", U.S. Appl. No. 10/390,202, filed Mar. 17, 2003.

Bertolino et al., "Medical Balloon", U.S. Appl. No. 10/263,225, filed Oct. 2, 2002.

Alt et al., "Vascular Stent with Composite Structure for Magnetic Resonance Imaging Capabilities", U.S. Appl. No. 09/779,204, filed Feb. 8, 2001.

H. Samavati et al., "Fractal Capacitors", IEEE Journal of Solids-State Circuits, vol. 33(12), Dec. 1998, 2035-2041.

J. Zou et al., "Development of Wide Tuning Range MEMS Tunable Capacitor for Wireless Communication Systems", Technical Digest, Intl Electron Devices Meeting, 2000, 403-406.

Z. Bashir et al., "High modulus filaments of polyethylene with lamellar structure by melt processing; the role of the high molecular weight components", Journal of Materials Science, Nov. 1984, vol. 19(11), 3713-25. 18 refs.

Z. Bashir et al., "Stiff and strong polyethylene with shish kebab morphology by continuous melt extrusion", Journal of Materials Science, Nov. 1986, vol. 21(11), 3993-4002. 16 refs.

"Applications using Panipol® Conductive Polymers" Available Web Site: www.panipol.com/apps/apps.htm Polymers Retrieved from the internet prior to the filing of the application.

"Panipol® Products" Available Web Site: www.panipol.com/products/products.htm Retrieved from the internet prior to the filing of the application.

"Advantages using Panipol® Conductive Polymers" Available Web Site: www.panipol.com/adv/adv.htm Retrieved from the internet prior to the filing of the application.

"Technology Development" Available Web Site: www.panipol.com/tech/tech.htm Retrieved from the internet prior to the filing of the application.

Fractus, S.A., "Fractal Miniaturization in RF and Microwave Networks", The Technology of Nature®, 2001.

* cited by examiner

MEDICAL DEVICES VISIBLE BY MAGNETIC RESONANCE IMAGING

TECHNICAL FIELD

The invention relates to medical devices, such as catheters and guidewires, that are visible by magnetic resonance imaging (MRI).

BACKGROUND

Certain medical devices are inserted and/or implanted into the body of a patient to perform a medical procedure. Examples of these devices include catheters, guidewires, medical balloons, stents, and stent-grafts. When a device is advanced through the body, its progress is preferably monitored, e.g., tracked, so that the device can be delivered properly to a target site. After the device is delivered to the target site, the device is preferably monitored to determine whether it has been placed properly and/or is functioning properly.

One method of monitoring a medical device is magnetic resonance imaging (MRI). MRI is a non-invasive technique that uses a magnetic field and radio waves to image the body. In MRI procedures, the patient is exposed to a magnetic field, which interacts with certain atoms, e.g., hydrogen atoms, in the patient's body. Incident radio waves are then directed at the patient. The incident radio waves interact with atoms in the patient's body, and produce characteristic return radio waves. The return radio waves are detected by a scanner and processed by a computer to generate an image of the body, thereby providing information about the placement and/or the functioning of the medical device.

SUMMARY

Medical devices adapted to be advanced through a patient and that are visible by magnetic resonance imaging (MRI) are described. In some embodiments, the devices include one or more features, such as contrast agent(s), that enhance the visibility of the devices under other monitoring or tracking methods, such as X-ray fluoroscopy and/or ultrasound spectroscopy. The visibility enhancing feature(s) can form a characteristic pattern that can be easily detected, e.g., by a pattern recognition system. The feature(s) allow the devices to be monitored in real time, e.g., during an interventional or intravascular procedure, to provide an indication that the devices are functioning properly.

In one aspect, the invention features a medical device having a conductive path, such as a spiral or a coil, capable of carrying a current. During use, a current is sent through the conductive path, which creates a weak local magnetic field that influences the gyromagnetic behavior of nearby atoms and their radiofrequency (RF) signals. The RF signal can be detected and processed to provide an indication of the position of the medical device. Alternatively or in addition, an alternating current is sent through the conductive path to create an RF signal that is directly receivable by an MRI system. Incident radio waves from the MRI system can also induce an RF signal from the conductive path, and the induced RF signal can be detected and processed to provide an indication of the position of the medical device. In some cases, the conductive path is defined by a conductive polymer or a thin conductive coating containing carbon. The medical device can further include one or more contrast agents arranged in a characteristic pattern to enhance the visibility of the device under different monitoring methods.

In another aspect, the invention features a medical device adapted for insertion into the body including an elongated shaft, and an electrically conductive path extending spirally about a portion of the shaft, wherein the conductive path is capable of being connected to a current source.

Embodiments may include one or more of the following features. The shaft includes an inner surface defining a lumen. The conductive path is defined by a conductive polymer (e.g., polyaniline and/or polypyrrole), conductive carbon (e.g., amorphous carbon and/or carbon nanotubes), and/or a metal (e.g., gold, platinum, tungsten, tantalum, silver, titanium, and/or copper). The conductive path has a thickness of less than about ten µm. A portion of the electrically conductive path is defined by a metal wire. The conductive path extends along an inner surface of the shaft. The electrically conductive path extends spirally in a first direction along the shaft, and extends spirally in a second direction counter to the first direction along the shaft. The shaft includes an electrically insulating layer (e.g., a polymer) between portions of the conductive path. The conductive path defines a series of coiled portions spaced from each other. The conductive path defines a band between the coiled portions.

The medical device can further include a capacitor electrically connected to the conductive path, the conductive path and the capacitor forming an LC circuit. The capacitor can be a fractal capacitor. The LC circuit can have a resonance frequency tuned to a MRI frequency of the body tissue. The LC circuit can have a resonance frequency tuned to a Larmor frequency of hydrogen.

The medical device can further include a MRI contrast agent. The MRI contrast agent can include a $T_1$ relaxation agent, such as one including gadolinium. The MRI contrast agent can include a material capable of generating a magnetic susceptibility artifact, such as a superparamagnetic material, a paramagnetic material, a ferromagnetic material, and/or a diamagnetic material. The MRI contrast agent can be encapsulated in a lumen, a hollow fiber, a microporous material, a mesoporous material, a nanoporous material, a channel, and/or a cavity. The MRI contrast agent can be embedded in a material of the device. The device can further include a coating (e.g., a polyurethane, a polyacrylic acid, and/or an acrylamide) that includes the MRI contrast agent. The device can further include an air-filled cavity. The device can further include a plurality of contrast agents (e.g., a $T_1$ relaxation agent, a material capable of generating a magnetic susceptibility artifact, a radiopaque material, and/or an ultrasound visible portion) arranged in a regular pattern.

The device can be a catheter, such as a guide catheter, a balloon catheter, a tumor ablation catheter, an aneurysm catheter, a urology catheter, or a perfusion catheter.

The medical device can be a polymeric guide wire. The guide wire can include polyethylene, for example, one having a Young's modulus of greater than about 10 GPa and/or a tensile strength of greater than about 0.5 GPa. The device can be a sheath introducer.

In another aspect, the invention features a medical device adapted for insertion into body tissue. The device includes a polymeric shaft having an inner surface defining a lumen; and an electrically conductive path extending spirally about the polymeric shaft and on the inner surface of the polymeric shaft. A portion of the conductive path is defined by a first conductive coating, wherein the conductive path is capable of being connected to a current source. The conductive path can cover substantially the entire inner surface of the polymeric shaft.

In yet another aspect, the invention features a medical device adapted for insertion into the body including a polymeric shaft having an inner surface defining a lumen, an electrically conductive path extending spirally about the polymeric shaft and on the inner surface of the shaft, wherein a first portion of the conductive path is defined by a conductive coating, and a second portion of the conductive path is defined by a metal wire. The second portion of the conductive path can extend on the inner surface of the shaft.

In another aspect, the invention features a medical device adapted for insertion into the body including a polymeric shaft having an inner surface defining a lumen; an electrically conductive path, a first portion of the path extending spirally in a first direction along the shaft, and a second portion of the path extending spirally in a second direction counter to the first direction along the shaft, the conductive path being defined at least in part by a conductive coating, and an insulating layer between the first and second portions of the conductive path.

In another aspect, the invention features a medical device including a first plurality of portions having a first contrast agent, and a second plurality of portions comprising a second contrast agent different than the first contrast agent, wherein the first and second pluralities of portions are arranged in a regular pattern.

Embodiments may include one or more of the following features. The first contrast agent can be a $T_1$ relaxation agent or a material capable of generating a magnetic susceptibility artifact. Portions of the first plurality can alternate with the portions of the second plurality. The device can further include a third portion capable of generating a signal void. The device can further include a radiopaque portion or a portion that is visible by ultrasound spectroscopy.

In another aspect, the invention features a medical device including a first plurality of portions having a first contrast agent, and a second plurality of portions capable of generating a signal void, wherein the first and second pluralities of portions are arranged in a regular pattern. The first contrast agent can include a $T_1$ relaxation agent or a material capable of generating a magnetic susceptibility artifact. Portions of the first plurality can alternate with the portions of the second plurality.

The details of embodiments of the invention are set forth in the accompanying drawings and the description below. Other aspects, features, and advantages of the invention will be apparent from the description and drawings, and from the claims.

DETAILED DESCRIPTION

Figure 1:
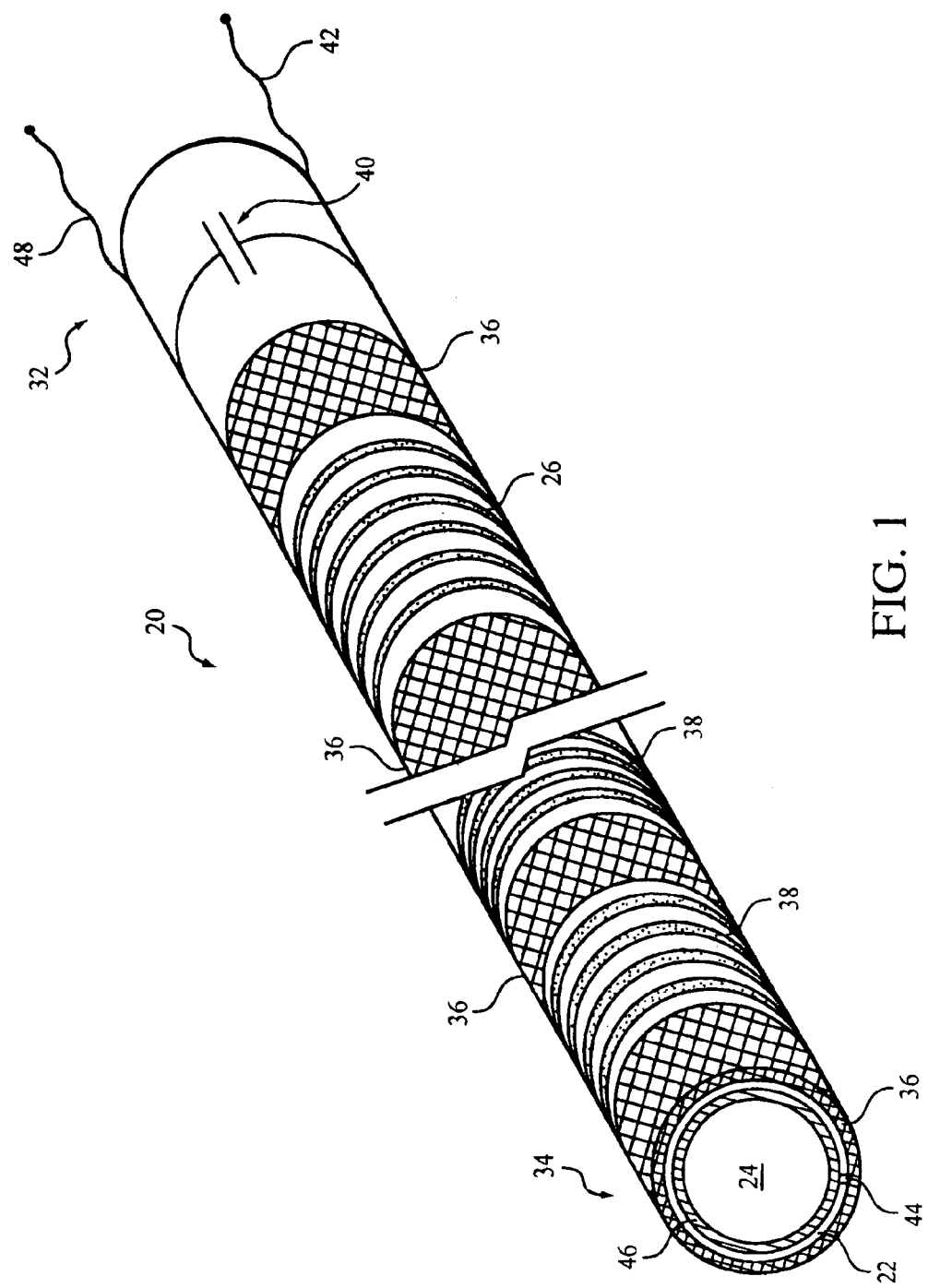
FIG. 1 is an illustration of a medical device.
Figure 2:
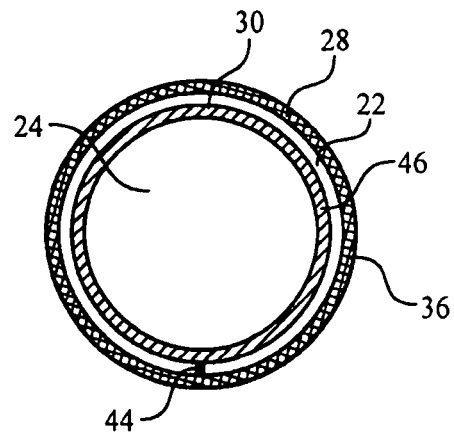
FIG. 2 is a cross-sectional view of the device of FIG. 1, taken along the distal end of the device.

Referring to FIG. 1, a medical device 20 (as shown, a tubing or a catheter) includes an elongated shaft 22 and a conductive path 26 formed on the shaft. Referring as well to FIG. 2, shaft 22 has an exterior surface 28 and an interior surface 30 that defines a lumen 24. Conductive path 26 is disposed on exterior surface 28 and interior surface 30, extending from a proximal end 32 to a distal end 34 of device 20. As shown, conductive path 26 includes a plurality of alternating solid portions or bands 36 and coil portions 38 extending on exterior surface 28 and along the length of shaft 22. Near proximal end 32, conductive path 26 includes a capacitor 40 and terminates with an electrical lead 42. At distal end 34, conductive path 26 extends across a conductive bridge 44 to interior surface 30, where the conductive path includes a solid conductive portion 46 that serves as a return path for flowing current (described below). Solid portion 46 extends proximally and terminates with an electrical lead 48. Leads 42 and 48 are capable of being connected to a current source (not shown).

As described below, during use, when leads 42 and 48 are connected to a current source and current is passed through coil portions 38 (which acts as an inductor) and capacitor 40 (which together to the inductor forms an LC circuit), the visibility of medical device 20 can be actively enhanced for magnetic resonance imaging (MRI). For example, in an MRI-processed image, coil portions 38 can appear as a characteristic pattern, such as a series of bright portions, that can be easily detected and distinguished by eye or by a detection system from surrounding body tissue.

Still referring to FIG. 1, shaft 22 can be formed of one or more materials, such as non-magnetic materials, that do not interfere with the MRI visibility of device 20. The material can be visibly transparent or opaque. Examples of materials include polymers, such as, for example, polypropylene, polyethylene (such as high density polyethylene), polysulfonate, polyamide (e.g., Nylon), polyethyleneterephthalate (PET), polytetrafluoroethylene (PTFE), polyacetonitrile, polymer-amorphous carbon composites, and polymer-carbon nanotube composites. The polymers can be extruded to form a flexible shaft that can navigate a tortuous path. Other polymers that can be used, including additives such as compatibilizers, and methods of making a tube or a catheter (e.g., a multilayer tube or catheter) are described in commonly-assigned U.S. Ser. No. 10/645,014, entitled "Medical Devices" and filed on Aug. 21, 2003. Examples of non-polymer materials include ceramics, glass, or non-ferromagnetic metals, such as aluminum and titanium.

In some embodiments, conductive path 26 includes a thin coating of one or more conductive materials. Examples of materials include conductive polymers, such as polyaniline, polypyrrole, or poly(ethylene-dioxythiophene) (PEDT), and conductive carbon (e.g., graphite). Syntheses of conductive polymers are described in the literature. Conductive polymers are also available commercially, for example, polyaniline from Panipol (Porvoo, Finland), polyaniline- and polypyrrole-coated carbon powders as well as highly soluble emeraldine base (EB) from Eeonyx Corp., polypyrrole dispersions having different core materials from DSM, and PEDT from H. C. Starck. Other materials include metals having low magnetic susceptibility, such as copper, silver, gold, platinum, tungsten, tantalum, titanium, or alloys of these materials. The material can be radiopaque, e.g., visible by X-ray fluoroscopy. Examples of radiopaque materials include tantalum, tungsten, gold, platinum, palladium, or their alloys. The coating of material(s) can have a thickness of about ten nanometers to about 20 micrometers, although larger thicknesses can be formed. By forming the coating thin, the conductive path can be formed to enhance the MRI visibility of device 20, while not compromising (e.g., degrading) the mechanical properties of the device. In certain cases, such as balloon catheters, having a relatively thick coating can increase the rigidity of the catheter. As a result, the catheter may not be able to travel well through a narrow and tortuous path.

Conductive path 26 can be formed using any of a variety of techniques. For example, certain conductive polymers can be dissolved in an organic solvent or dispersed in aqueous or non-aqueous media, and then applied (e.g., casted, sprayed or painted) to form a pre-selected pattern. Other techniques include plating, dipping, spraying, sputtering, plasma deposition, chemical vapor deposition, physical vapor deposition, or pulse laser deposition (PLD). Selected patterns of conductive path 26 can be formed, for example, by covering selected portions of shaft 22 with a mask (such as an adhesive tape or a dissolve material (e.g., polysaccharide, gelatin, or polyvinyl alcohol (PVA))) prior to forming the conductive path, and subsequently removing the mask after the path is formed. Another technique is to form a complete, uniform coating and subsequently remove selected areas to form conductive path 26, e.g., using excimer laser ablation. Another technique is to use conductive polymeric fibers or textile to form conductive path 26.

Figure 3:
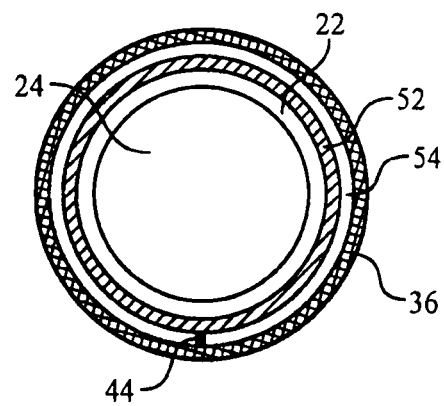
FIG. 3 is a cross-sectional view of a medical device.
Figure 4:
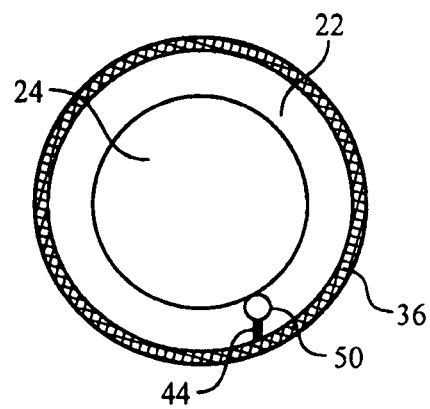
FIG. 4 is a cross-sectional view of a medical device.

Other configurations of conductive path 26 can be formed. Referring to FIG. 3, a conductive layer 52 (e.g., a conductive polymer or conductive carbon) can be applied to shaft 22 to serve as a current return path. Subsequently, an insulating layer 54 can be applied to conductive layer 52. Insulating layer 54 can include a polymer (e.g., a heat shrink polymer such as a polyolefin, polytetrafluoroethylene (PTFE), polyamide (e.g., Nylon), polyvinyl chloride (PVC), or polyterephthalate (PET)) or a ceramic. Conductive path 26 can be completed by forming bands 36 and coil portions 38 on insulating layer 54. In some cases, bands 36 and/or coil portions 38 can be covered, e.g., with a protective polymer coating, to prevent damage to conductive path 26. Conductive layer 52 or solid portion 46 can cover substantially all of their respective adjacent surfaces or only a portion thereof, e.g., as a stripe extending to proximal end 32. In other embodiments, referring to FIG. 4, solid portion 46 can be replaced with a conductive wire 50 (e.g., a copper wire) that extends along the length of shaft 22 (e.g., from distal end 34 to proximal end 32 to lead 48). Wire 50 can be embedded in shaft 22 (as shown) or be disposed on (e.g., glued to) interior surface 30. Wire 50, or a stripe of solid portion 46 or conductive layer 52, can extend linearly or helically (e.g., counter to the direction of coil portions 38) to proximal end 32.

Figure 5:
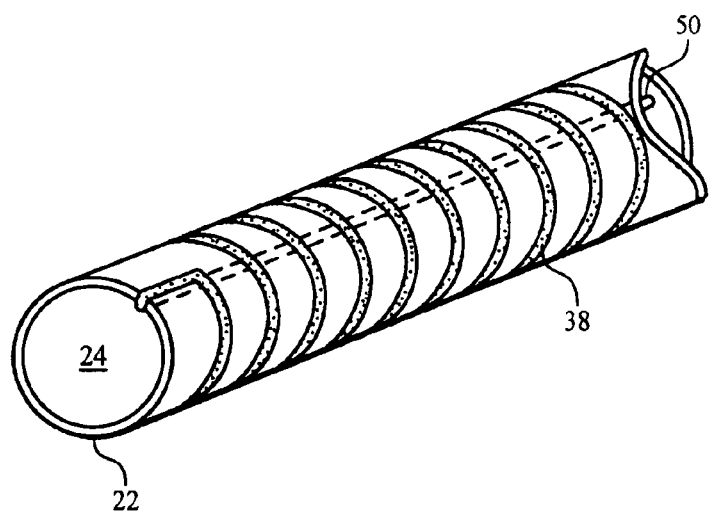
FIG. 5 is an illustration of a medical device.
Figure 6:
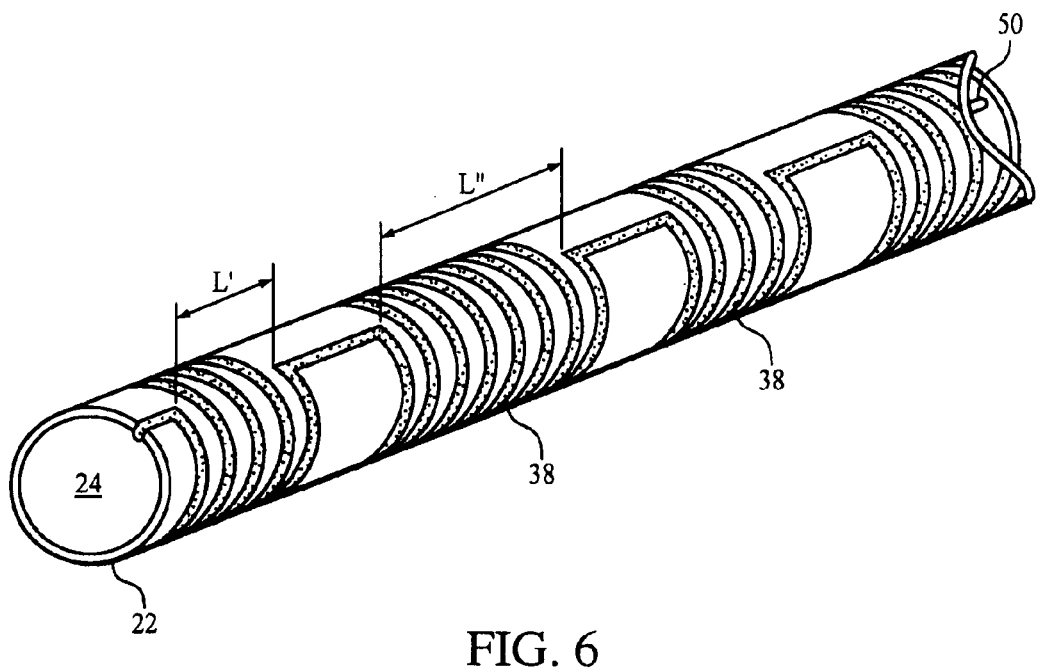
FIG. 6 is an illustration of a medical device.

Other configurations of bands 36 and/or coil portions 38 are possible. In some embodiments, a conductive path does not include any bands. Referring to FIG. 5, one coil portion 38 can extend the entire length of a device or at a selected portion of the device. Multiple, spaced coil portions 38 can extend the entire length of a device or at selected portions of the device. The length (L) of coil portions 38 and/or bands 36 can be same or different (as shown in FIG. 6). The spacing between coil portions 38 and/or bands 36 can be the same or different. Different configurations of bands and/or coil portions can affect the mechanical properties (such as flexibility and resistance to kinking) of the medical device.

To form a complete circuit, bridge 44, capacitor 40, and leads 42 and 48 are connected to conductive path 26. Bridge 44 can be formed using an electrically conducting epoxy or by applying one or more of the electrically conducting materials described above using any of the above techniques. An example of capacitor 40 is one having a capacitance of about 10.2 pF for a circuit to resonate at 64 mHz with an inductance, L, of about $6 \times 10^{-7}$ Henry. In some embodiments, to reduce any adverse effect on the mechanical performance of device 10, capacitor 40 is a fractal capacitor (e.g., as described in Samavati et al., "Fractal Capacitors" *IEEE Journal of Solid-State Circuits*, Vol. 33, No. 12, December 1998, p. 2035-2041). Capacitor 40 can be a component of the current source. Capacitor 40, such as those available from Fractus, S. A. (Barcelona, Spain), can be attached (e.g., glued) to device 20 near proximal end 32 and electrically connected to conductive path 26. The LC circuit can be a serial LC circuit or a parallel LC circuit. In some cases, a resistor is included in the LC circuit to lower the Q-value and broaden the magnetic resonance signal generated by the conductive path 105. Leads 42 and 48 can be connected to conductive path 26 at proximal end 32 using, for example, a conductive epoxy or solder.

In operation, device 20 is inserted into a subject (e.g., a human patient), and the subject is placed into an MRI system. The MRI system is capable of imaging the subject (e.g., body tissue) according to conventional methods, as described, for example, in U.S. Pat. No. 6,280,385. Additionally, during operation, a current is passed through conductive path 26, for example, sequentially or simultaneously with the pulsing of the incident radio waves. As current is passed through the circuit, in particular, through coil portions 38, the current induces a local magnetic field in the coil portions. The magnetic field generates a magnetic resonance signal (e.g., equal to the resonance frequency of the applied field from the MRI system) that can be detected processed by the MRI system. The MRI system is capable of processing the signals from device 20 and from the subject, superimposing the signals, and generating an image of both the device and the subject, thereby providing a real time indication of the position of device 20.

Other variations can be used. In some embodiments, the amount of current applied can be varied to enhance the visibility of device 20 according to the MRI system or sequence being used.

The LC circuit can also be tuned to change the resonance frequency of the loop circuit and facilitate detection of device 20 over a range of magnetic field strengths (e.g., 0.5 T, 1.5 T, and 3.0 T). For example, the resonance frequency can be changed by adding or removing one or more additional capacitors connected between leads 42 and 48, in parallel with capacitor 40. The additional capacitor(s) can be a part of one or more modular units adapted to engage (e.g., click and lock) with the proximal end of the catheter.

In other embodiments, the resonance frequency can be changed by short circuiting one or more coil portions 38 (e.g., with a conductive strip). A coil portion can be short circuited by contacting (e.g., sliding) a tube or C-clamp having a conductive inner surface over the coil portion. As the tube or C-clamp is slid over the coil portion, portions of (or the entire) coil portion is short circuited, which changes the inductance of the coil portion and the overall LC resonance frequency. The short circuiting can occur incrementally as a function of the number of windings in a coil portion, e.g., in ten discrete steps for a coil portion having ten windings. In other embodiments, the tube or C-clamp includes an inner surface having a conductive coil of different pitch than the windings of the underlying coil portion. Sliding the tube or C-clamp over a coil portion short circuits only parts of the coil portion, thereby allowing the inductance of the coil portion to be changed in finer increments.

The capacitor(s) described herein can be microelectromechanical systems (MEMS) tunable capacitor(s). MEMS tunable capacitors are described, for example, in Zou et al., *Development of a Wide Tuning Range MEMS Tunable Capacitor for Wireless Communications Systems*, Technical Digest—International Electron Devices Meeting 2000. p. 403-406. The MEMS tunable capacitor allows the capacitance value of the capacitor to be changed automatically. For example, the information from an MRI image can be used by a processor to directly update the capacitor continuously to enhance the resonance frequency of the system. The MRI system can detune or tune the LC circuit to enhance the visibility of the catheter by enhancing the contrast in real time.

Still in other embodiments, a direct current is passed through conductive path 26 that induces a magnetic field, which disturbs the local spin behavior to provide a detectable signal.

Alternatively or in addition, the radio wave pulses from the MRI system can cause the LC circuit to resonate at the magnetic resonance frequency, thereby providing a passive (i.e., no applied current) method of imaging device 20, as described in Melzer, et al., U.S. Pat. No. 6,280,385. Briefly, when incident radio wave pulses strike coil portions 38, a magnetic field is induced within the coil portions. The induced magnetic field in turn generates an eddy current that flows to capacitor 40, where the current is temporarily stored. When the incident radio wave pulses are paused, the current stored in capacitor 40 flow to coil portions 38, where the current now produces a local magnetic field with a magnetic resonance signal (e.g., at the magnetic resonance frequency of the MRI system). The MRI system is capable of detecting the signal from the LC circuit, processing the data to provide an image of device 20, and superimposing the images of the device and the subject to produce an image of the device in the subject on a visual display. As a result, real time imaging of device 20 can be performed.

OTHER EMBODIMENTS

In certain embodiments, such as when a direct current is passed through conductive path 26, device 20 does not include a capacitor.

In other embodiments, device 20 can include one or more agents that can further enhance MRI visibility, and/or enhance fluoroscopic and/or ultrasound visibility of the device. The agent, sometimes called a contrast agent, can be in the form of, e.g., a neat liquid, particles, a solution, a hydrogel, or an emulsion. The agent can have an MRI response that is different than the MRI response of the medical device in which the contrast agent is used, and/or the MRI response of the bodily tissue or fluid near the contrast agent during use. The MRI response is the response to a magnetic field or radio waves used during MRI. In some embodiments, the contrast agent includes one or more materials having a $T_1$ relaxation time that is different than that of the medical device and/or tissue. For example, the contrast agent can include a material that appears bright in an MRI image, such as a solution having a $T_1$ (longitudinal) relaxation time shortening agent and a proton-containing fluid, such as water or glycerin. Examples of $T_1$ relaxation time shortening agents include a paramagnetic metal salt or a paramagnetic metal chelate compound, such as heavy metal complexes, e.g., gadolinium diethylenetriaminepentaacetic acid (e.g., a 1% Gd-DTPA aqueous solution), GdDTPA-BMA, and GdHP-D03A (e.g., available from Schering, Nycomed and Bracco under the trade marks MAGNEVIST®, OMNISCAN®, and PROHANCE®).

Alternatively or in addition, the contrast agent can include one or more materials that produce a magnetic susceptibility artifact (i.e., an artifact marker that appears dark in an MRI image). The material can have a T2 relaxation time that is different than that of the medical device and/or tissue. For example, the contrast agent can include a carrier or a fluid having ferromagnetic, ferrimagnetic, or superparamagnetic nanoparticles, such as iron oxide, dysprosium oxide, and/or gadolinium oxide. The particles can be surface modified, e.g., made hydrophilic, to suspend the particles in the fluid and reduce the occurrence of precipitation and/or coagulation. Examples of particles and methods of modifying the particles are described in U.S. Pat. Nos. 6,123,920 and 6,423,296, hereby incorporated by reference. A magnetic susceptibility artifact can also be introduced into the MRI image by including an air-filled cavity in the medical device, e.g., in shaft 22.

The contrast agent can be embedded into shaft 22. For example, the contrast agent can be encapsulated in hollow members, such as hollow fibers, and dispersed in the shaft as described in commonly-assigned U.S. Ser. No. 10/390,202, filed Mar. 17, 2003. The contrast agent can be contained in a cavity or a lumen defined by the medical device, and/or by supported on a porous material, such as a ceramic material (e.g., aluminum oxide, titanium oxide, or a zeolite). Solid contrast agents can be blended into a structural material of device 20 (e.g., a polymer of shaft 22) and extruded to form the device. The contrast agent can be applied directly to the surface of the device, e.g., as a neat material or in the presence of solvent. In embodiments, the contrast agent can be mixed with an adhesive (such as a polyurethane adhesive) and applied to the surface as a coating, e.g., from about 50 to about 300 microns thick.

Alternatively or in addition, the MRI contrast agent can be incorporated into a coating composition and coated onto a surface of the medical device. The coating can be on an interior surface and/or on the exterior surface of a medical device. Forming the coating on an interior surface can reduce loss of the contrast agent by fluid exchange (e.g., with bodily fluid), thereby enhancing the effective lifetime of the contrast agent. The contrast agent can be incorporated into a coating using methods such as compounding or blending.

The coating composition can include a lubricous, hydrophilic and/or hydrogel material used to improve biocompatibility and to aid insertion of the device through the body. Hydrophilic and hydrogel polymers include, e.g., polyethylene oxide, polypropylene oxide, polyvinyl-pyrrolidone, polycarboxylic acid, cellulosic polymers, gelatin, maleic anhydride polymers, polysaccharides, polyvinyl alcohol, polyacrylic acid, hyaluronic acid, collagen, and poly(2-hydroxyethyl methacrylate) (polyHEMA). For example, Gd-DTPA can be dissolved in water and mixed with a 1% polyacrylic acid/polyacrylamide hydrogel solution. The mixture (a hydrogel/Gd-DTPA complex) can be attached to a device by covalent bonding. Such methods are described in U.S. Ser. No. 09/995,528, filed Nov. 27, 2001.

Methods for applying coatings to medical devices include, for example, dip coating and spraying. The surface of the medical device may be pre-treated in order to affix the coating to the surface of the device and/or enhance the hydrophilicity of plastic substrates prior to coating. Surface treatment techniques include, e.g., plasma activation, silanization, and treating the surface with a primer solution. Hydrophilic polymers can be integrated or attached to the device by co-extruding with the shaft. The polymer of the shaft provides desirable mechanical properties while the hydrophilic polymer loaded with a contrast agent provides magnetic resonance contrast.

Chemical and/or physical cross-linking of the coating may be used, depending on the type of coating, to prevent the coating from sloughing off or leaching from the surface of the device during insertion and/or contact with the surrounding body fluids. Cross-linking can be achieved, for example, by using chemical or radiation-based (e.g., photochemical and electron beam) techniques.

In some embodiments, the coating includes a releasable therapeutic agent, a drug, or a pharmaceutically active compound. Examples of agents include antithrombogenic agents, antiproliferative agents, antioxidants, anti-inflammatory agents, anesthetic agents, anti-coagulants, and antibiotics. Other agents, drugs, and compounds are described in U.S. Ser. No. 10/232,265, filed Aug. 30, 2002.

Figure 7:
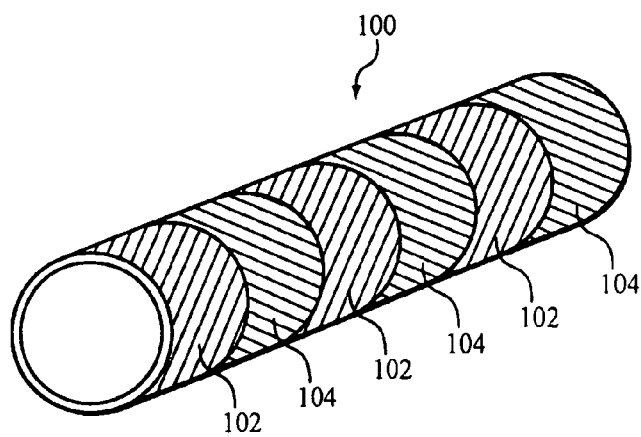
FIG. 7 is an illustration of a medical device.

The contrast agents can be formed on a medical device (such as shaft 22) in a predetermined sequence that can be easily recognized and distinguished from the surrounding body tissue under MRI, for example, using a pattern recognition system such as a pattern recognition software integrated in MRI software by the manufacturer. For example, referring to FIG. 7, a device 100 can include a series of bands 102 having a $T_1$ relaxation time shortening agent alternating with a series of bands 104 having a susceptibility artifact generating material, i.e., in an AB sequence that gives a characteristic alternating bright and dark MRI image. The device can have a portion with no contrast agent that would produce an absence of an MRI signal (i.e., a signal void) because of displaced bodily fluid. Sequences such as ABA, BAB, ABBA, or ABC are possible, where A can be a $T_1$ relaxation time shortening agent, B can be an artifact generating material or a signal void, and C is a marker or contrast agent different than A or B.

Figure 8:
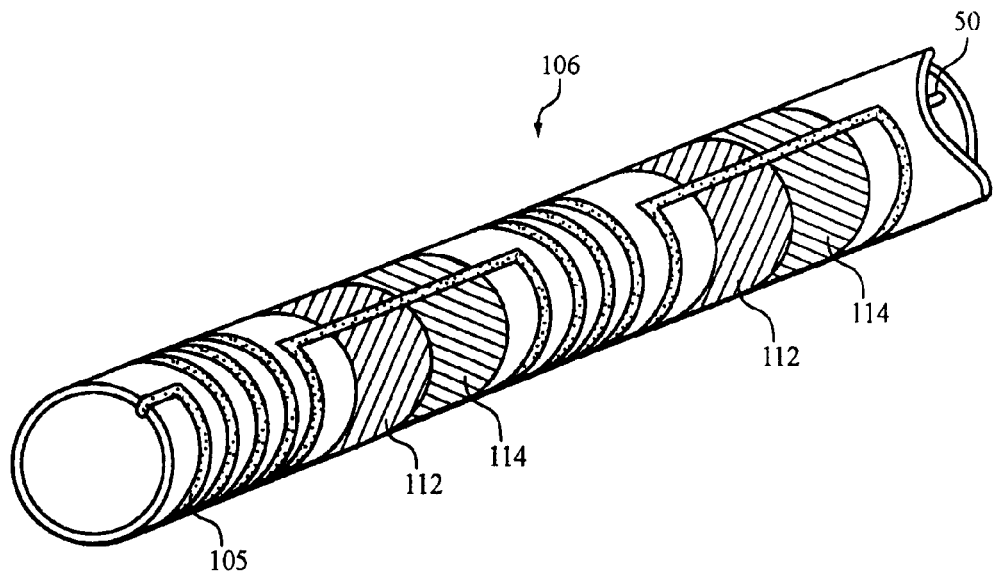
FIG. 8 is an illustration of a medical device.

The MRI contrast agents can also be included in a medical device having the conductive path or LC circuit described above. Referring to FIG. 8, a device 106 includes an electrically conductive path 105 that extends spirally about a portion of the shaft 110. In addition, a plurality of marker bands 112 and 114 are arranged along the length of the catheter shaft 110. Marker bands 112 include a magnetic susceptibility artifact marker, and marker band 114 includes a $T_1$ enhancing material. Marker bands 112 and 114 can be arranged in a characteristic pattern as described above. By having both an active visibility enhancing system (i.e., conductive path 105) and a passive visibility enhancing system (marker bands 112 and 114), device 106 can be monitored using different visualization techniques, thereby enhancing the versatility of the device. In other embodiments, device 106 includes one or more signal void portions and/or one of the other types of contrast agents described below.

The devices described herein can include other types of contrast agents, such as those visible by X-ray fluoroscopy (i.e., a radiopaque material) and/or ultrasound spectroscopy. Examples of radiopaque materials include tantalum, tungsten, platinum, palladium, or gold. The radiopaque material can be placed inside an encapsulating member (for example, as described in U.S. Ser. No. 10/390,202) and/or compounded with the material of the medical device. Alternatively or in addition, the radiopaque material, e.g., a band of radiopaque material, can be placed on a medical device at selected positions to make up a characteristic pattern. The ultrasound contrast agent can be any material that enhances visibility during ultrasound imaging. An ultrasound contrast agent can include a suspension having trapped bubbles of sufficient size to deflect sound waves.

Any of the medical devices described above can include a coiled portion or an inductive element, an MRI contrast agent, a radiopaque material, and/or an ultrasound contrast agent, in any combination or arrangement (e.g., ABCD or ABCDE). A combination of inductive elements, MRI contrast agents, ultrasound contrast agents, and/or radiopaque materials can offer the flexibility of visualizing a medical device under a variety of imaging conditions.

Figure 9:
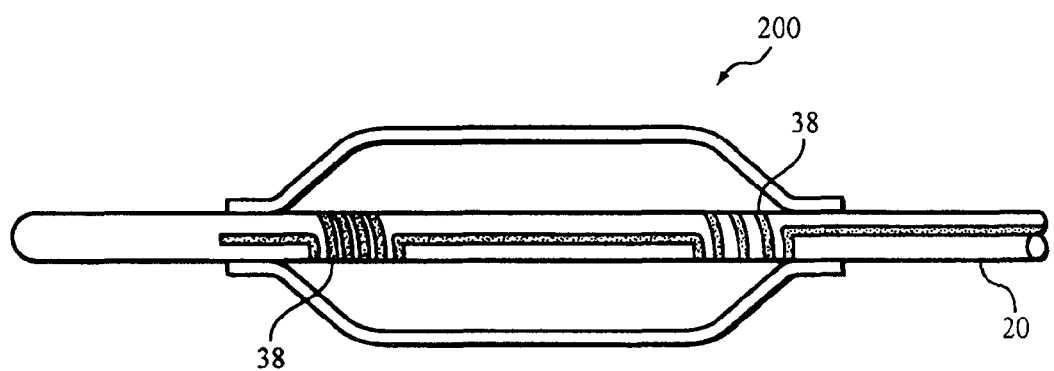
FIG. 9 is an illustration of a balloon catheter.

The tubing described above can be sized and shaped to form other devices. For example, referring to FIG. 9, device 20 can be attached to a medical balloon 200 to form into a balloon catheter (e.g., as described in commonly-assigned U.S. Ser. No. 10/263,225, filed Oct. 2, 2002, and entitled "Medical Balloon"; Anderson U.S. Pat. No. 6,120,364; Wang U.S. Pat. No. 5,714,110; and Noddin U.S. Pat. No. 4,963,313). Coil portions 38 can be used, for example, as markers that indicate the position of the balloon upon full inflation. Other examples of catheters into which the tubing can be formed include guide catheters (e.g., as described in U.S. Pat. No. 6,595,952), tumor ablation catheters, aneurysm catheters, urology catheters, and perfusion catheters (e.g., as described in U.S. Pat. No. 6,503,224). The tubing can be formed into an introducer sheath or a restraining sheath for a stent delivery system, for example, as described in U.S. Pat. No. 6,488,694. Methods of making tubing are described, for example, in U.S. Ser. No. 10/645,014, filed Aug. 21, 2003.

In other embodiments, the conductive path and/or marker (s) (e.g., MRI visible markers) described above can be incorporated into a guidewire, such as a polymeric guide wire. Some metal guide wires can absorb energy from the high power radiowave frequency energy used during MRI procedures. As a result, some metal guide wires can become hot, which can limit their use in MRI applications. Polymeric guide wires, in comparison, do not exhibit localized heating under MRI. Methods of making polymeric guide wires, including examples of materials, are described in U.S. Pat. No. 6,436,056, and U.S. Ser. No. 10/645,014, filed Aug. 21, 2003.

In some embodiments, the guidewire includes a biocompatible polymer, such as polyethylene, e.g., high-density polyethylene (HDPE), which can form fibers having a good mechanical profile. The HDPE polymer can have an average molecular weight ($M_w$) of about 400,000 g/mol, and a molecular weight distribution (i.e., polydispersity) of about 3 to 7, for example, a polydispersity of about 5. The polymer can have a high molecular weight tail (e.g., 0-10% content of greater than about 1,000,000) to ensure the formation of extended chain crystals. A minimal amount ($\leq 0.1\%$) of low molecular weight (e.g., 4000 g/mol or less) fraction is preferred to prevent the premature onset of relaxation processes in the melt and to ensure force transfer during extrusion of the melt through a die. Low molecular weight fractions can be removed by extraction in an appropriate solvent (e.g., hexane) to increase the tensile module of the resulting fiber. Examples of HDPEs are commercially available from, e.g., BASELL (BASF) Corporation under the trade designation LUPULEN 52 ZHI; Chevron Philips Corporation under the trade designation MARLEX TR-751; and Solvay Corporation under the trade designations RIGIDEX HM5420 XPH, AH 5493, and BH 5363.

A polymeric guide wire can be prepared, for example, by extrusion. The polymer can be extruded to form relatively stiff fibers having the requisite mechanical properties (e.g., Young's modulus (E) of greater than about 10 GPa and a tensile strength of greater than about 0.5 GPa). HDPE fibers can be prepared by solid-state extrusion of melt crystallized spherulitic polyethylene or by drawing solution crystallized gel films (e.g., performed by DSM (Heerlen, The Netherlands) as a process marketed as the Dyneemag Process). An alternative process involves melt deformation of HDPE under controlled conditions to obtain highly oriented fibers. The process involves chain extension of the high molecular weight fraction of HDPE having a linear macromolecular structure during flow just above the solidification temperature, followed by crystallization (e.g., of a high molecular weight fraction) and by co-crystallization e.g., of a low molecular weight fraction) of the remaining material. The polymer can be extruded at a temperature close to the crystallization temperature (e.g., a self-blocking temperature, which can be indicated by an extrusion pressure rise, e.g., upward from about 3500 psi) and at a strain rate of about $10^3$ $s^{-1}$ to solidify the deformed macromolecules before relaxation occurs. In some cases, crystallization occurs from about $T_g+30$ to about $T_m-10$ (e.g., from about 140 to about 160° C.). Such processing conditions can create an elongated, interlocking morphology that displays exceptional mechanical properties (e.g., a Young's modulus (E) of between about 10-80 GPa and a tensile strength of about 1.2 GPa). The fibrils can make up about 5% of the extruded material and can have a diameter of between about 5-25 nm with an aspect ratio of about 200-600. The bulk material can be characterized as a lamellar overgrowth chain direction like in the fibrils. An example of an extrusion apparatus is a mini-extruder (Axxon BX 12, D=12.5 mm, L/D=26) with a suitably designed die (e.g., opening angle 45°, 1 mm, 1/d 25). The extrusion head can be equipped with a pressure transducer and a thermocouple to control pressure and temperature during extrusion. Additional information regarding HDPEs is described in Bashir, Z., et al., *J. Mat. Science,* 19 (1984), 3713; and Bashir, Z., et al., *J. Mat. Science,* 19 (1986), 3993. In certain embodiments, the extrusion head is equipped with one or more transducers or vibrators. Vibratory energy (e.g., ultrasonic vibrations) from the transducer(s) can allow the extrusion temperature to be lowered by reducing friction between the polymer melt and the surface of the extrusion head. Examples of vibrators include mechanical transducers (e.g., spring mass/moving coil systems) or solid state transducers such as those having piezoelectric elements, available, e.g., from STAPLA Ultrasonics Corp. (Wilmington, Mass.) and Blatek Inc. (State College, Pa.).

All of the features disclosed herein may be combined in any combination. For example, the HDPE polymer described above can be used to make any of the devices described above. Each feature disclosed may be replaced by an alternative feature serving the same, equivalent, or similar purpose. Thus, unless expressly stated otherwise, each feature disclosed is only an example of a generic series of equivalent or similar features.

The following examples are illustrative and not intended to be limiting.

EXAMPLE 1

This example estimates how much field disturbance may be needed to make a visible marker.

For a coil portion like the coil portions shown in FIG. 1 with the axis of the coil portion along the central axis of the catheter, the magnetic field is created inside the coil portion and outside the coil portion along the direction of the axis of the coil. Since the polymer of the catheter is creating a void, the visible material by MRI is the water inside of the catheter. The field inside of the coil with multiple windings can be calculated by:

$$B = I \cdot (N/L) \cdot \mu_o$$

where $\mu_o$ is the permeability in a vacuum [$(\mu_o)$ =12.566370614×$10^{-7}$ H/m (of N/$A^2$)]; I is current in Ampere; and (N/L) is the number of windings per meter. Assuming that the artifact to be induced to be visible is similar to or greater than a typical fat-water chemical shift of 220 Hz at 1.5 T, then the field created inside the coil is 5.167×$10^{-6}$ T relative to the field outside the coil. So, for a coil having a length of five mm and wherein the width of the individual conductive paths is 100 micrometer, with a spacing of 50 micrometers (i.e., 33 windings over 5 mm gives a N/L of 6600), a current of 0.62 mA can be applied to obtain the targeted field.

EXAMPLE 2

Figure 10:
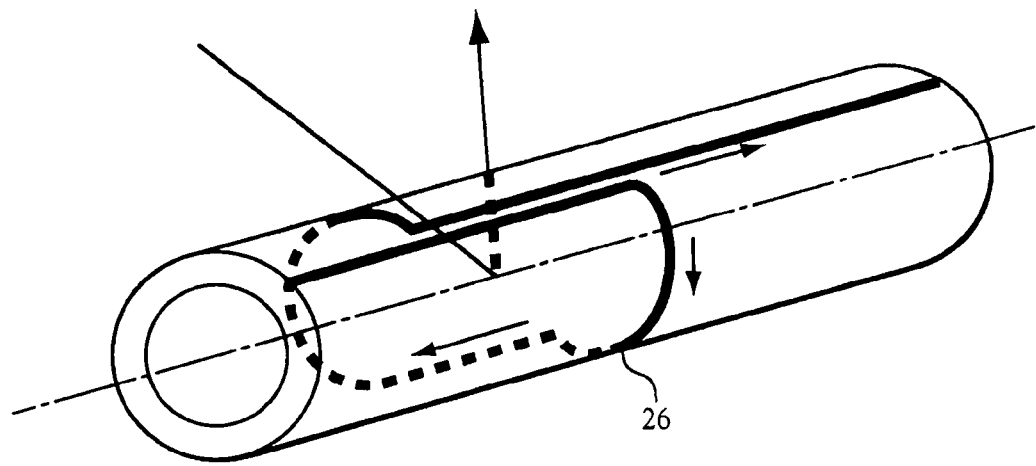
FIG. 10 is an illustration of a medical device.
Figure 11:
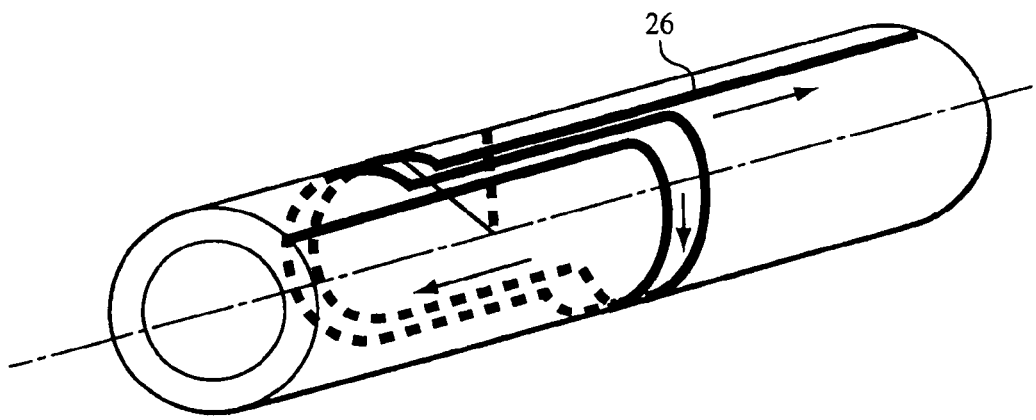
FIG. 11 is an illustration of a medical device.

Alternatively or in addition to having the coil portion(s) as shown in FIG. 1 (which is generating a field in the direction of the catheter axis), a medical device can include portions capable of generating a field at an angle with the catheter axis. FIGS. 10 and 11 show examples of coil portions capable of generating fields that can extend outside of the catheter tube and change the spin behavior, for example, of the water or blood, outside the catheter.

For a single coil as shown in FIG. 10, the field in the center of a single round loop is given by:

$$B_{z=0} = \mu_o I/(2R)$$

where $\mu_o$ is the permeability in a vacuum [$(\mu_O)$ =12.566370614×$10^{-7}$ H/m (of N/$A^2$)]; I is current in Ampere; and R is the radius of the loop.

The normalized B-field is given by the equation:

$$B_{rel} = \frac{B_2}{B_{z=0}} = \frac{b^3}{(b^2+z^2)^{3/2}} = \left(\frac{b}{\sqrt{b^2+z^2}}\right)^3$$

where b is the radius of the loop; z is the point of interest along the z-axis; and $B_{rel}$ is the ratio of the magnetic field at the point interest to the maximum magnetic field.

To create a visibility of at least two voxels, or volume elements, in the MRI image, a magnetic field of 5.167×$10^{-6}$ Tesla 0.8 mm outside the catheter tube is preferably created. For a tube having a diameter of 1.667 mm and in which the center of the winding lies at the center of the tube, the z value in the formula above is taken as 0.8 mm+(1.667/2) mm=1.653 mm. Therefore, $B_{rel}$(b=0.8335 mm, z=1.653 mm)=0.0913. So, B(z=0) is (5.167×$10^{-6}$/0.09127)Tesla=5.66×$10^{-5}$ T. Therefore, using $B_{z=0}=\mu_o I/(2R)$(R=0.8335×$10^{-3}$ m), I=75 mA. For the structure shown in FIG. 11, the magnetic field is twice as high, so 37.5 mA can be used.

All publications, applications, and patents referred to in this application are herein incorporated by reference to the same extent as if each individual publication or patent was specifically and individually indicated to be incorporated by reference in their entirety.

Other embodiments are within the claims.

What is claimed is:

1. A medical device adapted for insertion into the body, comprising:

an elongated shaft having a proximal end, a distal end and a central longitudinal axis;

an electrically conductive path extending spirally about a portion of the shaft, wherein the conductive path is capable of being connected to a current source;

wherein the conductive path defines a series of coiled portions spaced from each other and includes a series of non-coiled elements extending parallel to the elongate shaft wherein a first non-coiled element is disposed between a first coiled element and a second coiled element; and a plurality of contrast agents arranged in a regular pattern where the plurality of contrast agents alternate with the series of coiled portions;

wherein the contrast agents comprise a $T_1$ relaxation agent and a material capable of generating a magnetic susceptibility artifact wherein the $T_1$ relaxation agent is disposed in a first series of marker bands and wherein the material capable of generating a magnetic susceptibility artifact is disposed in a second series of marker bands, wherein the second series of marker bands has a different composition than the first series of marker bands and wherein the regular pattern includes the first series of marker bands alternating with the second series of marker bands.

* * * * *